(12) United States Patent
Childress

(10) Patent No.: US 11,806,438 B2
(45) Date of Patent: Nov. 7, 2023

(54) ULTRAVIOLET WAND

(71) Applicant: The Boeing Company, Chicago, IL (US)

(72) Inventor: Jamie J. Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/990,400

(22) Filed: Aug. 11, 2020

(65) Prior Publication Data

US 2022/0023477 A1 Jan. 27, 2022

Related U.S. Application Data

(60) Provisional application No. 63/055,789, filed on Jul. 23, 2020.

(51) Int. Cl.
| | | |
|---|---|---|
| *A61L 2/24* | (2006.01) | |
| *B64F 5/30* | (2017.01) | |
| *A61L 2/10* | (2006.01) | |
| *B25J 9/16* | (2006.01) | |
| *B25J 13/08* | (2006.01) | |
| *B25J 15/00* | (2006.01) | |

(52) U.S. Cl.
CPC ................. *A61L 2/24* (2013.01); *A61L 2/10* (2013.01); *B25J 9/1664* (2013.01); *B25J 13/089* (2013.01); *B64F 5/30* (2017.01); *A61L 2202/11* (2013.01); *A61L 2202/14* (2013.01); *A61L 2202/25* (2013.01); *B25J 15/00* (2013.01)

(58) Field of Classification Search
CPC .......... A61L 2/10; A61L 2/24; A61L 2202/11; A61L 2202/14; A61L 2202/25; B64F 5/30; B25J 15/00; B25J 9/1664; B25J 13/089
USPC ........................... 250/453.11, 454.11, 455.11
See application file for complete search history.

(56) References Cited

U.S. PATENT DOCUMENTS

| | | | |
|---|---|---|---|
| 2010/0104471 A1 | 4/2010 | Harmon et al. | |
| 2011/0054574 A1* | 3/2011 | Felix | A61N 5/06 250/493.1 |
| 2018/0064833 A1* | 3/2018 | Childress | B64D 11/02 |
| 2018/0161468 A1* | 6/2018 | Dayton | A61L 2/24 |
| 2018/0272016 A1* | 9/2018 | Hunt | A61L 2/10 |
| 2020/0215214 A1 | 7/2020 | Rosen et al. | |
| 2021/0145995 A1* | 5/2021 | Majdali | A61L 2/22 |
| 2021/0338854 A1* | 11/2021 | Nissenbaum | A61B 1/00117 |
| 2022/0008602 A1* | 1/2022 | Sood | A61L 2/10 |

OTHER PUBLICATIONS

Childress, J., Roberts, J., & King, T. (2020). Disinfection with Far-UV (222 nm Ultraviolet light). (Year: 2020).*
U.S. Appl. No. 16/987,493, filed Aug. 7, 2020.
U.S. Appl. No. 17/016,466, filed Sep. 10, 2020.
European Patent Application Serial No. 21186373.3, Search Report dated Dec. 22, 2021, 7 pgs.

* cited by examiner

*Primary Examiner* — Nicole M Ippolito
(74) *Attorney, Agent, or Firm* — Kwan & Olynick LLP

(57) ABSTRACT

Described herein is a decontamination device for use in vehicle applications. The decontamination device includes a device body and an ultraviolet (UV) light. The UV light includes a UV light source, coupled to the device body and configured to move relative to the device body. A plurality of openings is disposed around the UV light source.

20 Claims, 9 Drawing Sheets

ULTRAVIOLET WAND

CROSS-REFERENCE TO RELATED APPLICATIONS

This application claims the benefit under 35 U.S.C. § 119(e) of U.S. Provisional Patent Application No. 63/055,789, entitled "ULTRAVIOLET WAND" filed on Jul. 23, 2020, which is incorporated herein by reference in its entirety for all purposes.

BACKGROUND

Commercial aircraft include an interior cabin with various facilities, such as lavatories and galley kitchens. As can be appreciated, during a typical flight, various surfaces in these facilities become contaminated. For example, passengers and flight attendants contact door handles to access lavatories and, sometimes, sneezes in proximity to these handles. In short, during certain flights, a door handle and other like components end up covered with various contaminants, such as viruses, bacteria, and other like pathogens or microbial contaminants.

A conventional approach involves flight attendants periodically cleaning such surfaces. Furthermore, ground-based cleaning personnel conduct comprehensive decontamination between flights. However, in certain situations, there may not be sufficient time to effectively clean each touch surface, e.g., between two consecutive uses. Moreover, individual flight attendants may not thoroughly clean each surface or miss some surfaces. As such, various contaminants may remain on particular surfaces which may pose real and/or perceived health concerns to future passengers.

SUMMARY

Described are methods and systems for decontamination of vehicles. In certain examples, a decontamination device is described. The decontamination device includes a device body and an ultraviolet (UV) light. The UV light includes a UV light source, coupled to the device body and configured to move relative to the device body, with a plurality of openings are disposed proximate the UV light source.

In another example, a robot is described. The robot includes an end effector and a decontamination device, coupled to the end effector. The decontamination device includes a device body and an UV light. The UV light includes a UV light source, coupled to the device body and configured to move relative to the device body, with a plurality of openings are disposed proximate the UV light source.

Illustrative, non-exclusive examples of inventive features according to present disclosure are described herein. These and other examples are described further below with reference to figures.

BRIEF DESCRIPTION OF THE DRAWINGS

The disclosure may best be understood by reference to the following description taken in conjunction with the accompanying drawings, which illustrate various examples.

DETAILED DESCRIPTION

In the following description, numerous specific details are set forth in order to provide a thorough understanding of the presented concepts. The presented concepts may be practiced without some, or all, of these specific details. In other instances, well known process operations have not been described in detail to avoid unnecessarily obscuring the described concepts. While some concepts will be described with the specific examples, it will be understood that these examples are not intended to be limiting.

Introduction

Described herein is a decontamination device for use in vehicle applications. Decontamination of vehicles, such as commercial aircrafts, is often rather challenging due to various design and operational aspects. In certain examples, such vehicles include crevices and other places that are hard to reach through conventional cleaning techniques. Furthermore, for vehicles that are open to the public, quick cleaning turnaround is needed in order to maximum usage of the vehicles, so tools are often needed to be reconfigurable to avoid time lost in obtaining new tools. Sometimes, decontamination of the vehicle needs to be performed while passengers are present. The decontamination device described herein addresses such challenges.

Figure 9:
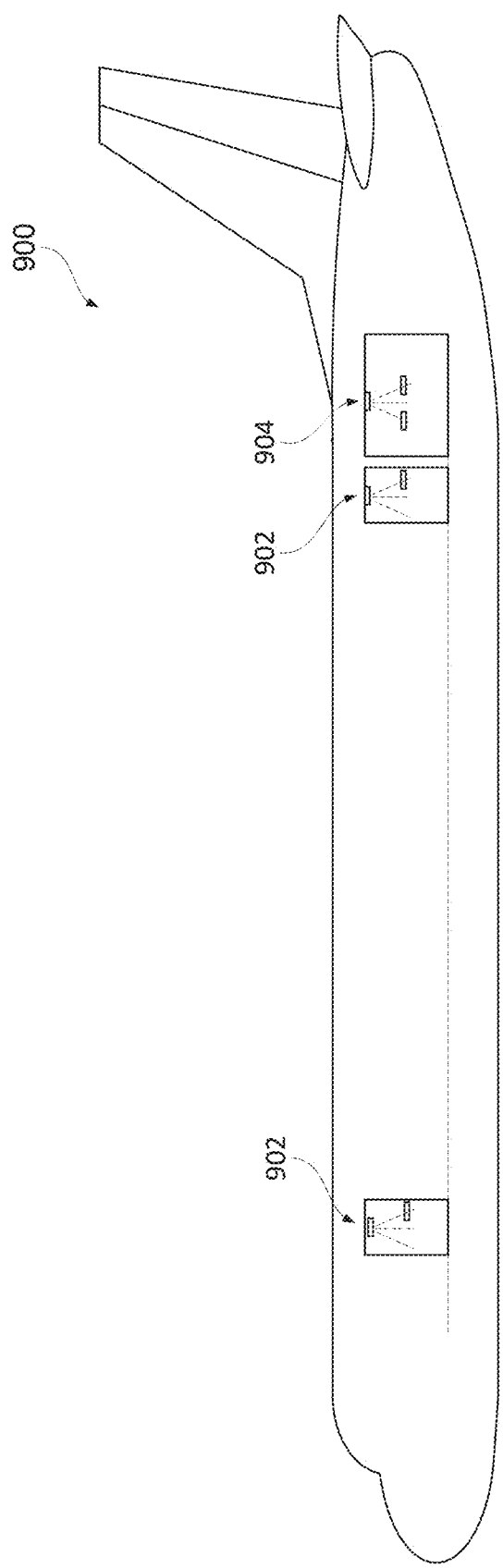
FIG. 9 is a schematic illustration of an aircraft, illustrating decontamination systems positioned in lavatories and galley kitchen of the aircraft, in accordance with some examples.

An example of such a vehicle to be decontaminated is illustrated in FIG. 9. FIG. 9 is a schematic illustration of aircraft 900, comprising lavatories 902 and galley kitchen 904, in accordance with some examples. Each of these facilities is used by multiple different people. For example, each lavatory 902 is often used by dozens of time during each flight, especially during long intercontinental flights. Furthermore, each of these facilities include multiple surfaces, which, in certain situations, are each contaminated via a direct contact (e.g., touch) or an indirect contact (e.g., sneezing, coughing). Some of these surfaces have complex geometries, which makes the decontamination process even more challenging.

Decontamination Device Examples

FIGS. 1-5 illustrate representations from various angles of decontamination devices, in accordance with some examples. FIGS. 1-5 illustrate decontamination device 100. Decontamination device 100 is configured to decontaminate surfaces on vehicles, such as aircraft 900, by destroying pathogens, in accordance with some examples. In various examples, decontamination device 100 is of a form factor appropriate for decontaminating various surfaces of vehicles. Thus, for example, decontamination device 100 is between 12 to 24 inches in length and includes a narrow form factor to fit into various nooks and crevices within a vehicle.

Decontamination device 100 includes device body 102, ultraviolet (UV) light 104, and battery 106. In various examples, device 102 and/or other portions of decontamination device 100 is constructed of plastic, composites, metals, fabric, leather, and/or other such appropriate materials. Battery 106 stores and provides electrical power for operation of decontamination device 100, such as power for operating UV light 104. Battery 106 is coupled to device body 102 or UV light 104. In certain examples, battery 106 is rechargeable and/or swappable. Thus, for example, battery 106 is configured to be decoupled from the rest of decontamination device 100 and a fresh battery swapped in to provide for more power for decontamination device 100.

Device body 102 is coupled to UV light 104. Device body 102, in certain examples, includes one or more controllers 122 (that includes one or more one or more single or multi-core processors and/or memories), data and/or power communication components 124 (e.g., batteries, wiring, and/or wired or wireless communications), user interface 120 (e.g., buttons, speakers, screens, touchscreens, and/or other such interfaces where commands are received from a user and/or information provided to the user), and/or other such components. In certain examples, device body 102 includes handle 112. Handle 112 is configured for a user of decontamination device 100 to hold decontamination device 100. Thus, the user passes their hand through handle 112 in order to grip decontamination device 100. In certain examples, handle 112 wraps all the way around an opening configured to contain a user's hand. Such a configuration minimizes the likelihood of decontamination device 100 slipping off of a user's hand and being lost in the various crevices of a vehicle.

In certain examples, device body 102 includes user interface 120 for operating UV light 104. For example, user interface 120 allows for the turning on/off of a light source of UV light 104, such as UV light source 108, for adjusting an intensity of UV light source 108, for changing an operating mode of UV light source 108, or for controlling UV light source 108 in another manner. User interface 120, in certain examples, is communicatively coupled to controller 122 via data and/or power communication components 124. Controller 122, in certain examples, receives input from user interface 120 and provides data controlling the corresponding response of decontamination device 100. Thus, controller 122 provides data to various portions of decontamination device 100 (e.g., via data and/or power communication components 124) to, for example, control operation of those various portions. Additionally, controller 122, in certain examples, provides various data to user interface 120 for user interface 120 to communicate to a user data directed to operation of decontamination device 100 to be communicated through visual, audio, and/or another manner by user interface 120). In certain additional examples, decontamination device 100 does not include a controller 122 and instead includes switches for controlling the flow of power from one or more batteries to UV light source 108.

In various examples, UV light 104 is configured to rotate, swivel, and/or extend (e.g., telescope) relative to device body 102. Thus, UV light 104, in various examples, is mounted on a hinge, a ball and socket connection, a telescoping device, a movable arm, and/or another such movable connection. As such, UV light 104 is able to be configured to shine UV radiation into areas that are not typically reachable.

As described, UV light 104 includes one or more UV light source 108. In various examples, UV light source 108 may be a light source configured to emit UV light (e.g., UV radiation within the UV light wavelengths). UV light source 108 is, in various examples, an incandescent bulb, one or more light emitting diodes, and/or another form of light that emits, at least, UV light in certain wavelengths, as further described herein.

The UV light emitted by UV light source 108 may include UV radiation in the UV subrange of, approximately, between 200 nanometers (nm) and 260 nm or more. Such UV radiation allow for decontamination of various surfaces by being directly or indirectly exposed to the UV radiation. In various examples, UV light source 108 generates UV radiation within shortwave ultraviolet-C (e.g., 100-280 nm), which is useful for germicidal irradiation, as well as light in other wavelengths.

In certain examples, UV light 104 additionally includes filter 114. Filter 114 is, in certain examples, configured to couple to UV light 104. Filter 114, in such examples, couples to UV light 104 through mechanical couplings such as tabs, snaps, fasteners, and/or other such mechanical techniques, through magnetic couplings, through adhesives, and/or through other techniques such as Velcro®. Thus, in such examples, filter 114 is configured to be attached and/or removed from one or more sides of UV light 104 as needed.

Filter 114 is a band pass, low pass, and/or other filter configured to allow for only, certain wavelengths of UV radiation to pass through. Thus, in a certain example, filter 114 is a low pass filter that allows for UV radiation of wavelengths shorter than approximately 225 to 245 nm (e.g., 230 nm or 240 nm) to pass through filter 114. In such examples, filter 114 only allows light that is, for example, 240 μm or shorter in wavelength to pass through. Without being restricted to any particular theory, it is believed that, in certain situations, this sub-240 nm range of UV radiation is particularly effective with pathogen decontamination while being safe to humans. As such, use of filter 114 allows for UV light 104 to be operated to disinfect surfaces while being safe to any persons around the area. Accordingly, decontamination device 100, when fitted with filter 114, is able to be used in areas with people that are not wearing UV protective equipment.

Figure 5:
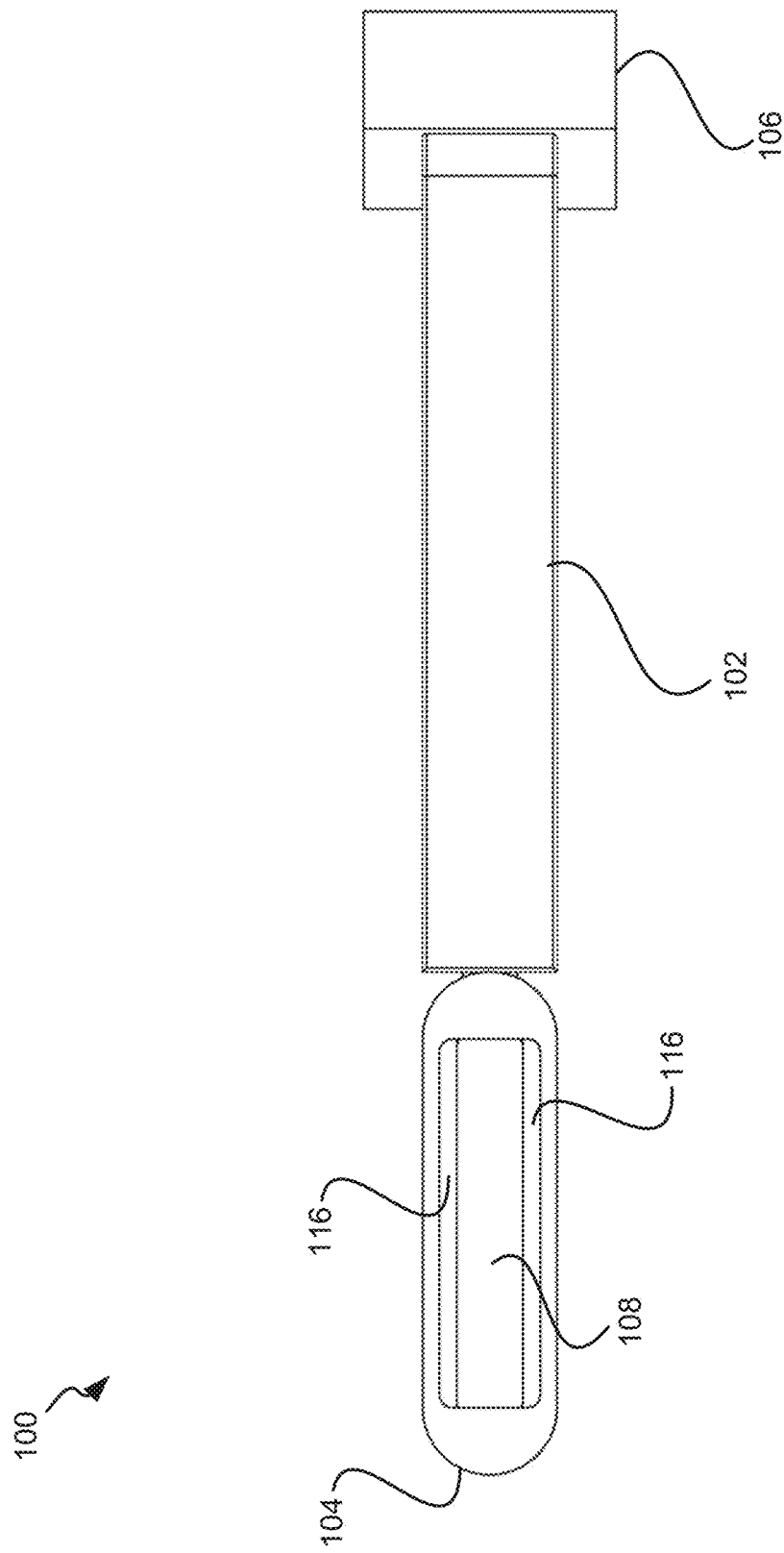

FIG. 5 shows that openings 116 are disposed around UV light source 108. As shown in FIG. 5, two openings 116 are disposed around UV light source 108, but other examples include any number of openings. Openings 116 are disposed proximate UV light source 108 to allow for reflected radiation to pass from first side 150 to second side 152, or vice versa. In certain examples, UV light source 108 include reflective finishes to further aid in the reflection of UV radiation.

Figure 2:
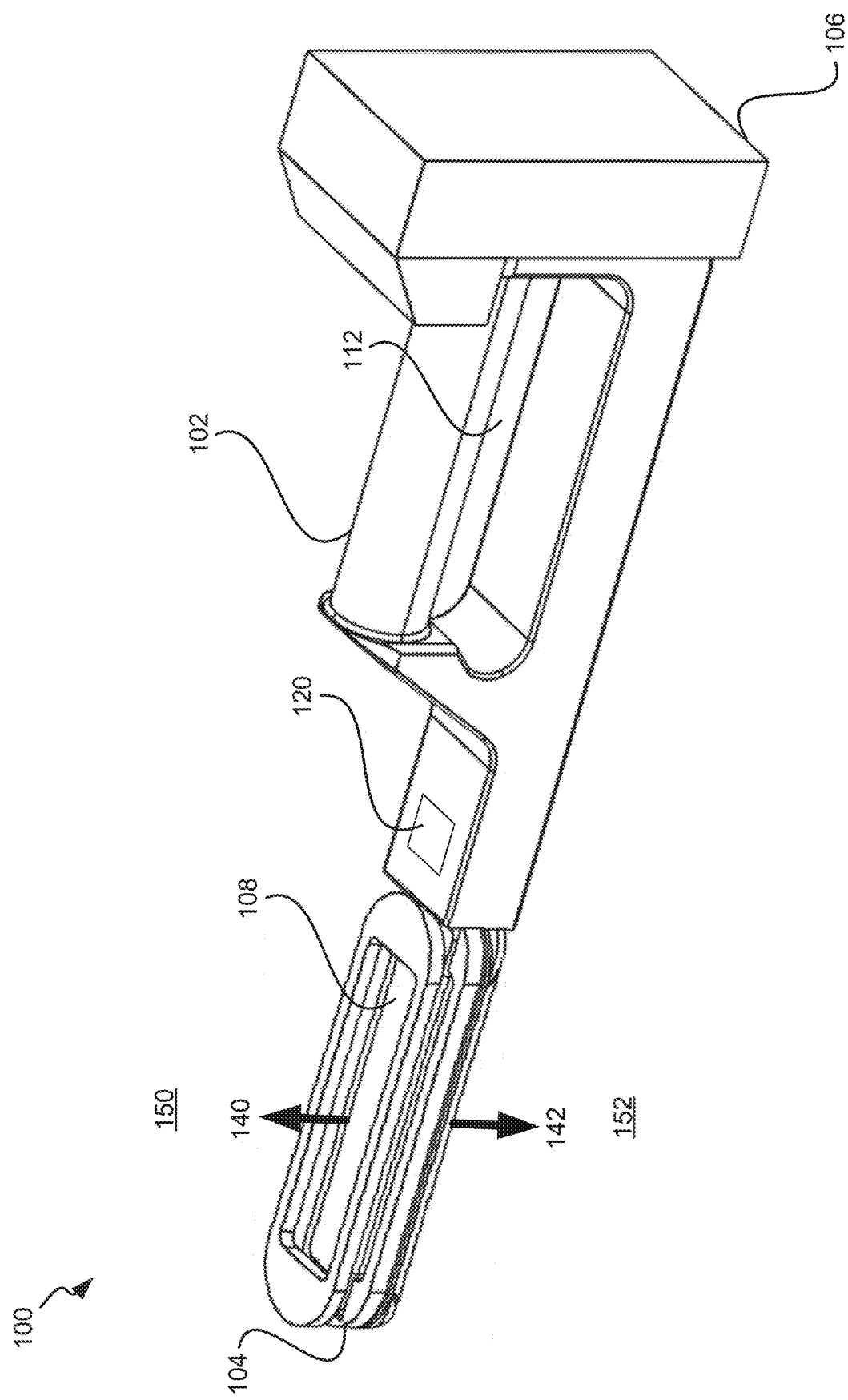
Figure 3:
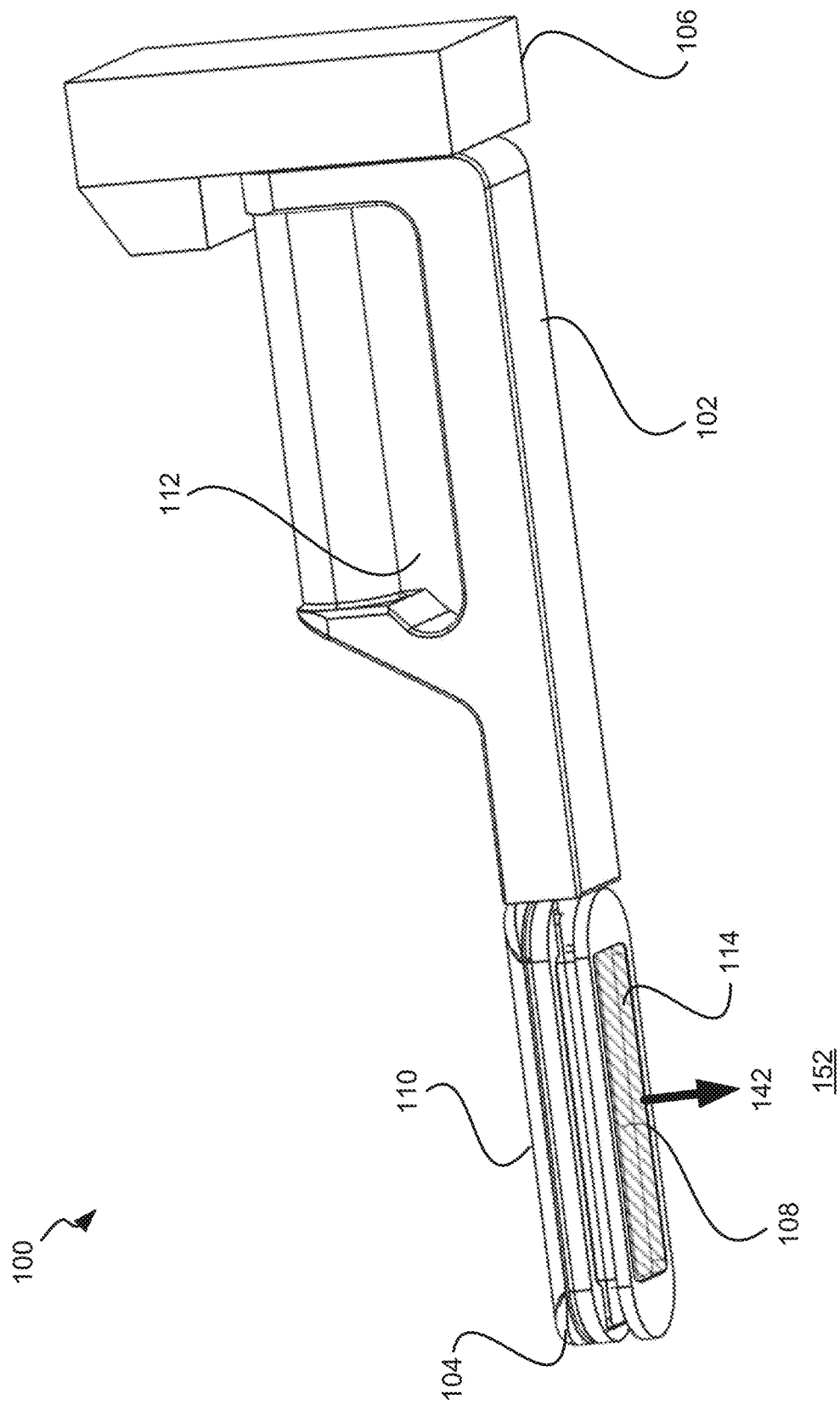
Figure 4:
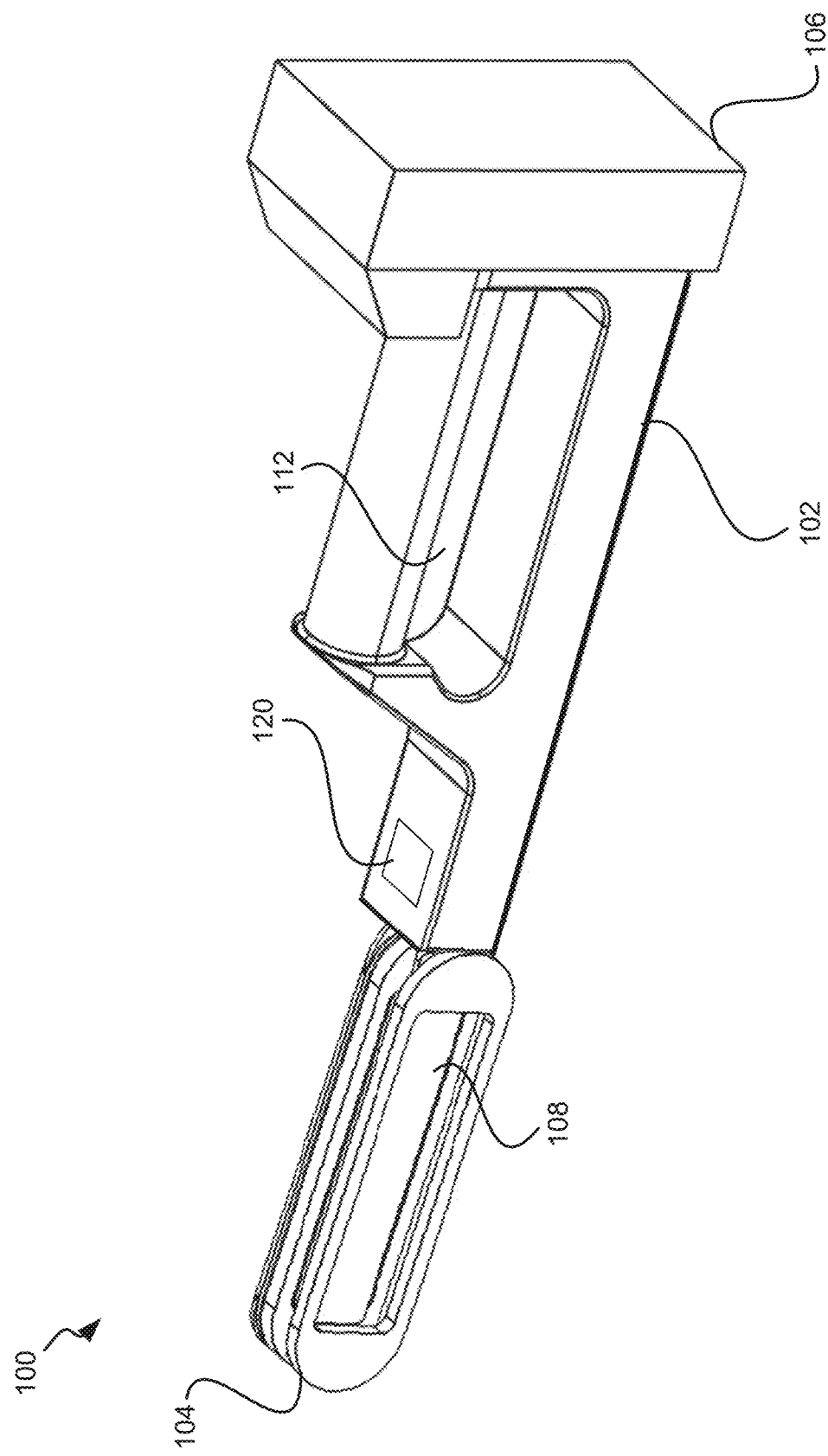

In various examples, UV light source 108 is configured to provide UV radiation in a plurality of directions, such as in directions 140 and 142 as shown in the example of FIG. 2, which includes UV light sources positioned on both first side 150 and second side 152 to emits UV light towards first side 150 and second side 152, respectively. In a certain example, directions 140 and 142 are opposite directions, but in other examples, UV light source 108 emits light in any number of directions.

Additionally, as shown in FIG. 5, reflector 110 is coupled to one or more sides of UV light 104 through, for example, mechanical couplings such as tabs, snaps, fasteners, and/or other such mechanical techniques, through magnetic couplings, through adhesives, and/or through other techniques such as Velcro®. Reflector 110 is configured to reflect the UV radiation emitted in direction 140 towards first side 150 to that of second side 152, increasing the intensity of UV radiation emitting in direction 142 towards second side 152. Thus, UV radiation generated on first side 150 of UV light 104 is reflected by reflector 110 through openings 116 towards second side 152 of UV light 104. Such a configuration allows for more effective sanitation of a surface by UV light 104 through increases in intensity of the UV radiation, Thus, use of reflector 110 allows for efficient sanitation when sanitation of only one surface or in only one direction is required.

In certain examples, UV light 104 includes filter 114 on a first side and reflector 110 on a second side. Such a configuration allows for the intensity of UV radiation output from one side of UV light 104 to be increased while filtering such light to be within desired wavelengths. Other configurations of UV light 104 include a plurality of filters 114 and/or reflectors 110 (e.g., disposed on both sides of UV light 104), As filter 114 and reflector 110 are configured to be coupled to and decoupled from MT light 104 as needed. UV light 104 is able to be configured as needed.

Decontamination Technique Example

Figure 6:
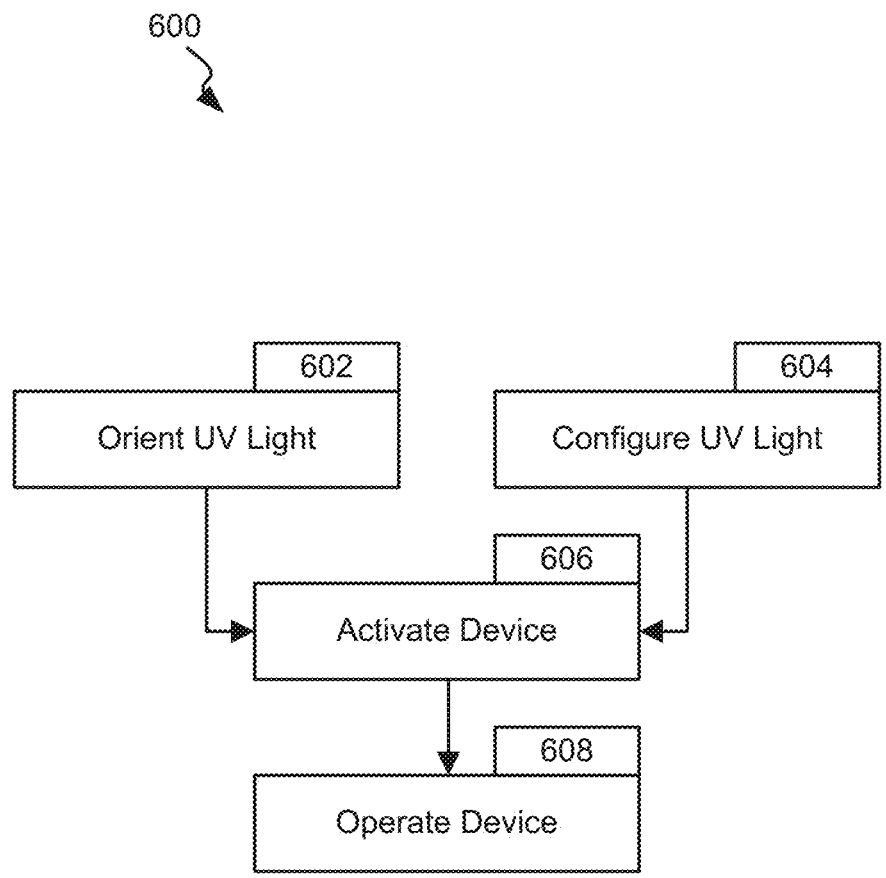
FIG. 6 is a process flow chart of a technique for utilizing a decontamination device, in accordance with some examples.

FIG. 6 is a process flow chart of a technique for utilizing a decontamination device, in accordance with some examples. Technique 600 of FIG. 6 is a technique for operating decontamination device 100, as described herein.

In 602, the UV light of the decontamination device is oriented, as needed. As the UV light is able to be rotated, swiveled, and/or extended as necessary, the user of the decontamination device is thus able to position the UV light as needed for the cleaning operation. Thus, for example, the user is able to position the UV light so that the UV light shines directly on a surface. In certain examples, the UV light is positioned by the user a recommended distance away from the surface.

Additionally, in 604, the UV light of the decontamination device is configured. Configuring of the UV light includes, in certain examples, setting the UV light at a certain intensity (e.g., power level), coupling one or more filters to the UV light, and/or configuring one or more reflectors to the UV light. For example, in certain applications, a reflector is coupled on a first side of the UV light to reflect UV light to a second side of the UV light. Alternatively or additionally, a filter is coupled to the second side of the UV light in order to filter the UV light emission to that of a desired wavelength.

Based on 602 and 604, the decontamination device is activated in 606. In certain examples, activation of the decontamination device is through the operation of one or more user interfaces such as an on-off button. The decontamination device is then operated to sanitize surfaces as needed in 608. Thus, for example, the decontamination device is held a certain distance away from a surface in order to sanitize the surface with UV light.

Vehicle Examples

Figure 7A:
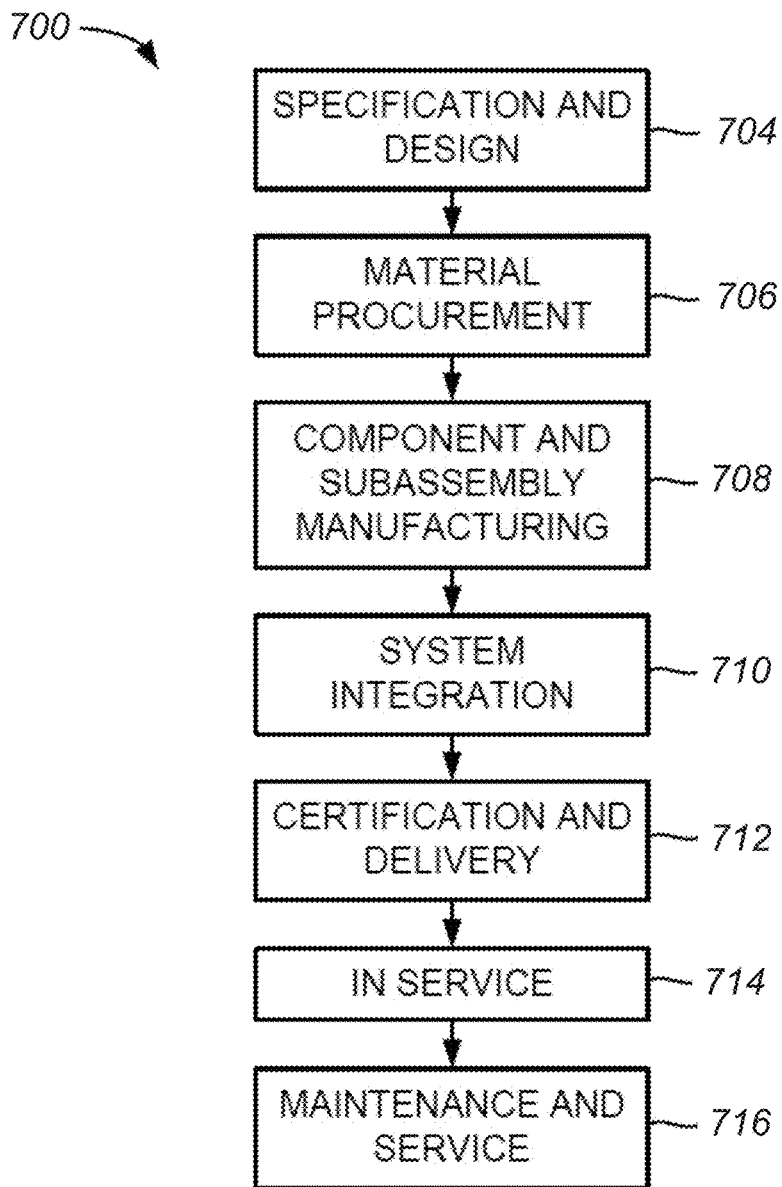
FIG. 7A is a process flowchart corresponding to a method for manufacturing and servicing the aircraft.
Figure 7B:
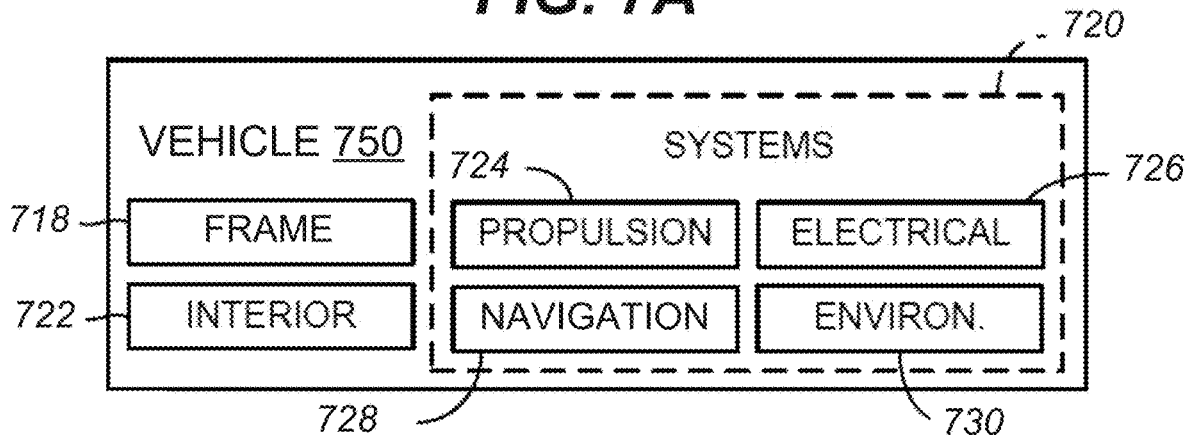
FIG. 7B illustrates a block diagram of an example aircraft, in accordance with some examples.

Examples of the disclosure is described in the context of a spacecraft manufacturing and service method 700 as shown in FIG. 7A and vehicle 750 as shown in FIG. 7B as applicable to such other contexts.

Figure 1:
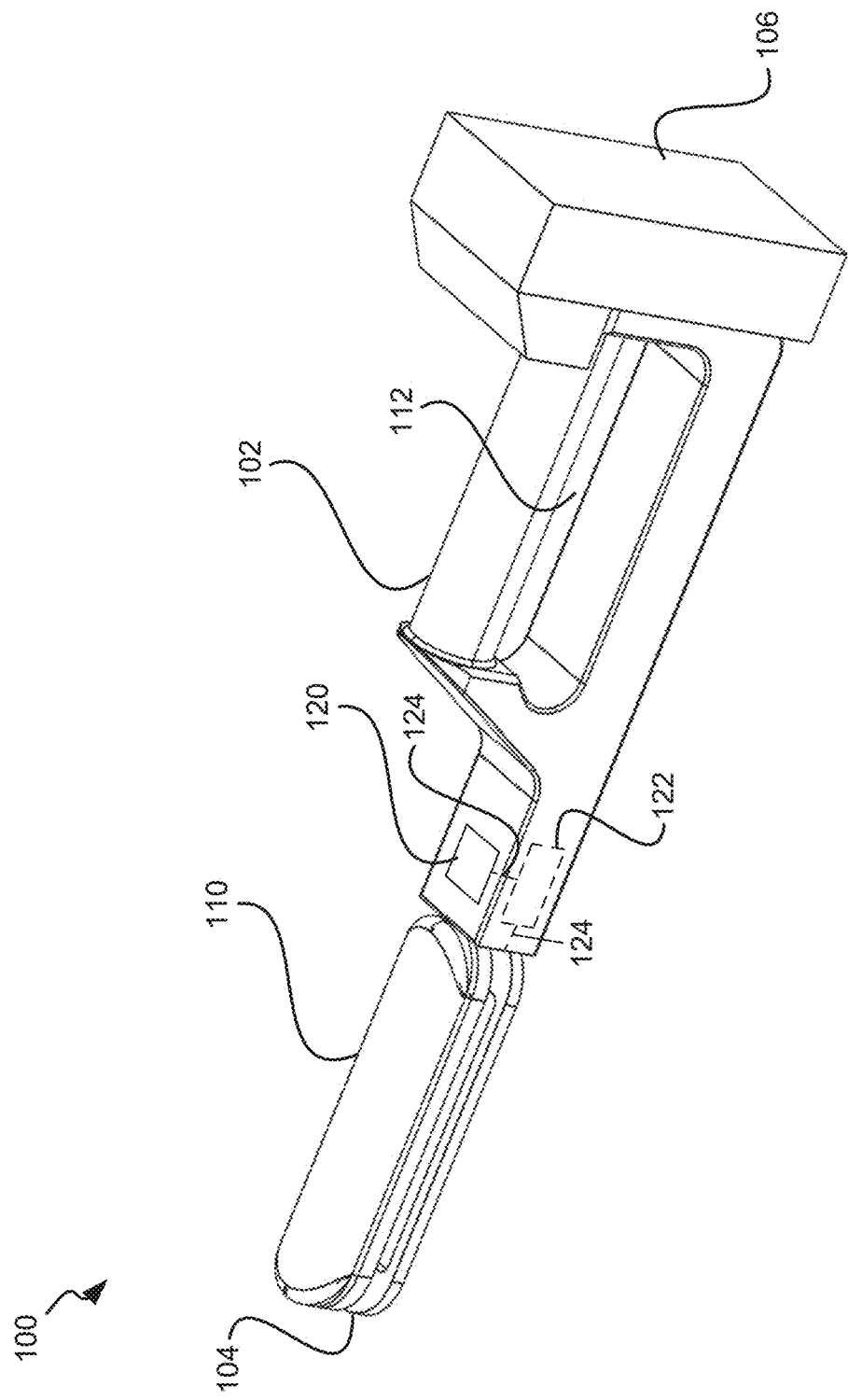
FIGS. 1-5 illustrate representations from various angles of decontamination devices, in accordance with some examples.

FIG. 7A illustrates a flow chart of an example of a vehicle production and service methodology, in accordance with some examples. In some examples, during pre-production, method 700 includes the specification and design 704 of vehicle 750 (e.g., a spacecraft as shown in FIG. 1) and material procurement 706. During production, component and subassembly manufacturing 708 and system integration 710 of vehicle 750 takes place. Thereafter, vehicle 750 goes through certification and delivery 712 in order to be placed in service 714. While in service, in certain examples, vehicle 750 is scheduled for maintenance and service 716 (e.g., modification, reconfiguration, refurbishment, and so on).

In certain examples, each of the processes of method 700 is performed or carried out by a system integrator, a third party, and/or an operator (e.g., a customer). For the purposes of this description, a system integrator includes any number of aerospace manufacturers and major-system subcontractors; a third party includes any number of venders, subcontractors, and suppliers; and an operator includes, in certain examples, an airline, leasing company, military entity, service organization, and so on.

FIG. 7B illustrates a block diagram of an example of a vehicle, in accordance with some examples. As shown in FIG. 7B, the vehicle 750 (e.g., a spacecraft) produced by method 700 includes frame 718 with plurality of systems 720, and interior 722. Examples of systems 720 include one or more of propulsion system 724, electrical system 726, navigation system 728, and environmental system 730. In various examples, other systems are also included within vehicle 750. Although an aerospace example is shown, the described principles are applicable to other industries, such as the automotive industry.

Robot Examples

Figure 8:
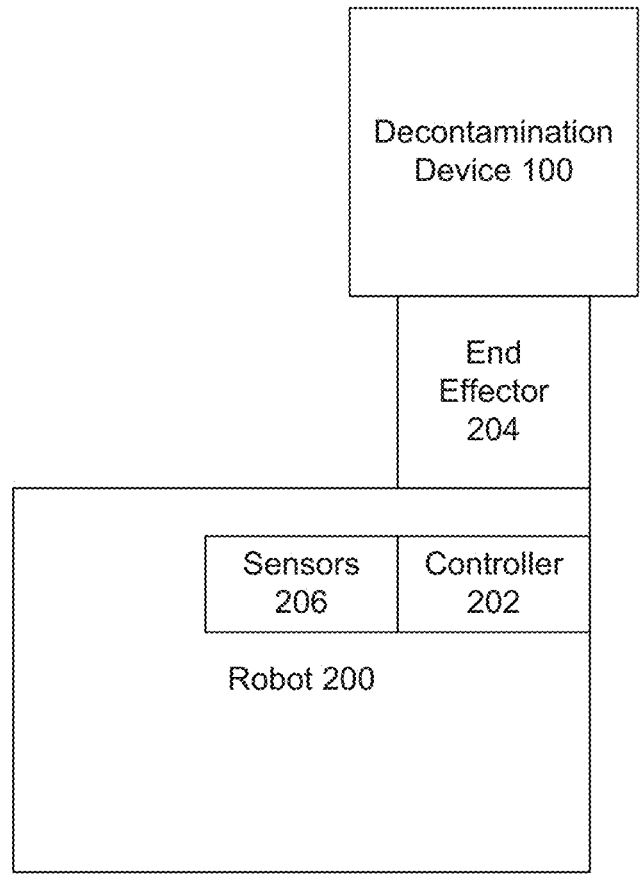
FIG. 8 illustrates a block diagram of an example robot, in accordance with some examples.

FIG. 8 illustrates a block diagram of an example robot, in accordance with some examples. FIG. 8 illustrates robot 200 that is configured to operate decontamination device 100 in, for example, the vehicles described herein. Thus, robot 200, in certain examples, is configured to decontaminate aircraft 900.

In various examples, robot 200 includes controller 202, end effector 204, and robotic sensors 206. End effector 204 includes one or more features, such as attachment points, that are configured to grip and/or couple to decontamination device 100. In certain examples, end effector 204 also includes one or actuators or other devices to move end effector 204 and/or decontamination device 100.

Operation of decontamination device 100 by robot 200 and/or end effector 204 is controlled by controller 202. In various examples, controller 202 includes one or more single or multi-core processors and memory to store instructions for operation of decontamination device 100 and/or end effector 204. In certain examples, controller 202 is configured to identify surfaces to be sanitized (e.g., through data from robotic sensors 206 of robot 200, which is configured to determine an environment around robot 200), move end effector 204 within a threshold distance of the surfaces to be sanitized, and/or guide decontamination device 100 to be positioned in hard to reach spots.

Further Examples

Further, the disclosure includes examples according to the following clauses:

Clause 1. A decontamination device 100, comprising:
a device body 102; and
an ultraviolet (UV) light 104, comprising:
a UV light source 108, coupled to the device body 102 and configured to move relative to the device body 102, wherein a plurality of openings 116 are disposed proximate the UV light source 108.

Clause 2. The decontamination device 100 of clause 1, wherein the UV light 104 is configured to rotate, swivel, and/or extend relative to the device body 102.

Clause 3. The decontamination device 100 of clause 1, wherein the UV light 104 is configured to couple to a reflector 110.

Clause 4. The decontamination device 100 of clause 3, further comprising the reflector 110, coupled to the UV light 104.

Clause 5. The decontamination device 100 of clause 4, wherein the UV light 104 comprises UV light sources disposed on a first side 150 and a second side 152, wherein the reflector 110 is coupled to the UV light 104 on the first side 150, and wherein the reflector 110 is configured to reflect UV radiation from the first side 150 towards the second side 152.

Clause 6. The decontamination device 100 of clause 5, wherein the openings 116 are configured to allow the reflected UV radiation to pass from the first side 150 to the second side 152.

Clause 7. The decontamination device 100 of clause 1, wherein the UV light 104 is configured to couple to a filter 114.

Clause 8. The decontamination device 100 of clause 7, further comprising the filter 114, coupled to the UV light 104.

Clause 9. The decontamination device 100 of clause 8, wherein the filter 114 is configured to filter out UV radiation of a wavelength longer than a threshold wavelength.

Clause 10. The decontamination device 100 of clause 9, wherein the threshold wavelength is 240 nanometers.

Clause 11. The decontamination device 100 of clause 7, wherein the UV light 104 is configured to couple to the filter 114 on a first side 150 of the UV light 104 and configured to couple to a reflector 110 on a second side 152 of the UV light 104.

Clause 12, The decontamination device 100 of clause 1, wherein the UV light source 108 comprises a reflective finish.

Clause 13. The decontamination device 100 of clause 1, wherein the device body 102 comprises a handle 112, and the decontamination device 100 further comprises a battery 106 coupled to the device body 102 and configured to power the UV light source 108.

Clause 14. The decontamination device 100 of clause 13, wherein the battery 106 is configured to decouple from the device body 102.

Clause 15. A robot 200, comprising:
an end effector 204; and
a decontamination device 100, coupled to the end effector 204, wherein the decontamination device 100 comprises:
a device body 102; and
an ultraviolet (UV) light 104, comprising:
a UV light source 108, coupled to the device body 102 and configured to move relative to the device body 102, wherein a plurality of openings 116 are disposed proximate the UV light source 108.

Clause 16. The robot 200 of clause 15, further comprising:
robotic sensors 206, configured to sense an environment proximate to robot 200.

Clause 17. The robot 200 of clause 16, further comprising:
a controller 202, configured to receive data from the robotic sensors 206 and operate the end effector 204.

Clause 18. The robot 200 of clause 17, wherein the controller 202 is configured to operate the end effector 204 by positioning the decontamination device 100.

Clause 19. The robot 200 of clause 15, wherein the UV light 104 is configured to rotate, swivel, and/or extend relative to the device body 102.

Clause 20. The robot 200 of clause 15, further comprising:
a filter 114 coupled to a first side 150 of the UV light 104; and
a reflector 110 coupled to a second side 152 of the UV light 104.

Conclusion

Although foregoing concepts have been described in some detail for purposes of clarity of understanding, it will be apparent that certain changes and modifications may be practiced within scope of appended claims. It should be noted that there are many alternative ways of implementing processes, systems, and apparatuses. Accordingly, present examples are to be considered as illustrative and not restrictive.

The invention claimed is:

1. A decontamination device, comprising:
a device body comprising a handle for a user to grasp, wherein the decontamination device is 12-24 inches in length and has a narrow form factor for fitting into crevices and nooks of a vehicle; and
an ultraviolet (UV) light, comprising:
a first UV light source disposed on a first side of the device body, and
a second UV light source disposed on a second side of the device body and that is opposite the first side,
wherein the first and second UV light sources are coupled to the device body and configured to move together relative to the device body,
wherein the first UV light source is operable to emit light in an opposite direction than light emitted from the second UV light source.

2. The decontamination device of claim 1, wherein the UV light is configured to rotate, swivel, and/or extend relative to the device body.

3. The decontamination device of claim 1, wherein the UV light is configurable to couple to an attachable reflector positioned over the first UV light source.

4. The decontamination device of claim 3, further comprising the attachable reflector positioned over the first UV light source.

5. The decontamination device of claim 4, wherein the attachable reflector is configured to reflect UV radiation from the first UV light source towards the second side to combine with UV radiation from the second UV light source.

6. The decontamination device of claim 5, wherein the UV light includes one or more openings arranged to allow the reflected UV radiation to pass from the first side to the second side.

7. The decontamination device of claim 1, wherein the UV light is configurable to couple to an attachable filter.

8. The decontamination device of claim 7, further comprising the attachable filter.

9. The decontamination device of claim 8, wherein the attachable filter is configured to filter out UV radiation of a wavelength longer than a threshold wavelength.

10. The decontamination device of claim 8, wherein the threshold wavelength is 240 nanometers.

11. The decontamination device of claim 7, wherein the UV light is configurable to couple to the attachable filter on the first side of the UV light and configurable to couple to a reflector on the second side of the UV light.

12. The decontamination device of claim 1, wherein the UV light source comprises a reflective finish.

13. The decontamination device of claim 1, wherein the device body comprises a handle, and the decontamination device further comprises a battery coupled to the device body and configured to power the UV light source.

14. The decontamination device of claim 1, wherein the battery is configured to decouple from the device body.

15. A robot, comprising:
an end effector; and
a decontamination device, coupled to the end effector, wherein the decontamination device comprises:
a device body comprising a handle coupled with the end effector, wherein the decontamination device is 12-24 inches in length and has a narrow form factor for fitting into crevices and nooks of a vehicle; and
an ultraviolet (UV) light, comprising:
a first UV light source disposed on a first side of the device body, and
a second UV light source disposed on a second side of the device body and that is opposite the first side,
wherein the first and second UV light sources are coupled to the device body and configured to move together relative to the device body,
wherein the first UV light source is operable to emit light in an opposite direction than light emitted from the second UV light source.

16. The robot of claim 15, wherein the controller is configured to operate the end effector by positioning the decontamination device.

17. The robot of claim 15, wherein the UV light is configured to rotate, swivel, and/or extend relative to the device body.

18. The robot of claim 15, further comprising:
a filter coupled to the first side over the first UV light source; and
a reflector coupled to the second side over the second UV light source.

19. The robot of claim 18, wherein the filter and reflector are attachable and removable.

20. The robot of claim 18, wherein the reflector is configured to reflect UV radiation from the first UV light source towards the second side to combine with UV radiation from the second UV light source.

* * * * *